United States Patent [19]
Jacobs

[11] Patent Number: 4,841,965
[45] Date of Patent: Jun. 27, 1989

[54] ANIMAL-HOLDING AND POSITION RESTORING DEVICE EMPLOYING VACUUM HOLDER AND MOUTHPIECE LEVEL

[76] Inventor: Deborah A. Jacobs, 173 Bonview St., San Francisco, Calif. 94110

[21] Appl. No.: 873,261

[22] Filed: Jun. 6, 1986

Related U.S. Application Data

[63] Continuation of Ser. No. 670,898, Nov. 13, 1984, abandoned.

[51] Int. Cl.⁴ .............................................. A61B 19/00
[52] U.S. Cl. .................... 128/303 B; 269/328; 378/208; 5/435
[58] Field of Search ................ 604/355, 346–349; 128/303 B, 133, 134; 269/328, 21; 351/245; 378/208, 209; 5/434–435, 436; 51/235; 294/64.1, 65

[56] References Cited

U.S. PATENT DOCUMENTS

| | | | |
|---|---|---|---|
| 1,719,982 | 7/1929 | Keith | 604/346 |
| 1,823,544 | 9/1931 | Howe | 604/346 |
| 2,565,381 | 8/1951 | Leighton | 33/221 |
| 2,758,375 | 8/1956 | Badovinac et al. | 32/19 |
| 2,913,833 | 11/1959 | Glintz | 34/97 |
| 3,025,397 | 3/1962 | Travis et al. | 250/50 |
| 3,154,683 | 10/1964 | Blair | 250/50 |
| 3,369,548 | 2/1968 | Moore et al. | 128/303 |
| 3,429,052 | 2/1969 | Hembd et al. | 33/220 |
| 3,514,606 | 5/1970 | Rabey | 250/65 |
| 3,783,863 | 1/1974 | Kliever | 128/134 |
| 3,794,314 | 2/1974 | Coburn et al. | 269/21 |
| 3,814,942 | 6/1974 | Darden | 250/456 |
| 3,851,644 | 12/1974 | Slagle | 128/134 |
| 4,058,112 | 11/1977 | Johnson | 128/1 R |
| 4,064,401 | 12/1977 | Marden | 250/456 |
| 4,096,637 | 6/1978 | Stade | 33/174 |
| 4,108,426 | 8/1978 | Lindstroem et al. | 269/328 |
| 4,193,002 | 3/1980 | Muether et al. | 250/479 |
| 4,256,112 | 3/1981 | Kopf et al. | 128/303 |
| 4,357,006 | 11/1982 | Hayes | 269/21 |
| 4,561,642 | 12/1985 | Parque | 269/21 |

FOREIGN PATENT DOCUMENTS

| | | | |
|---|---|---|---|
| 8103420 | 12/1981 | Int'l Pat. Institute | 128/352 |
| 543147 | 5/1956 | Italy | 128/361 |
| 1011517 | 12/1965 | United Kingdom | 604/347 |
| 1331587 | 9/1973 | United Kingdom | 128/361 |

Primary Examiner—Michael H. Thaler
Attorney, Agent, or Firm—David Pressman

[57] ABSTRACT

A head-immobilizing device for holding a patient's head, or other part of a patient's anatomy, rigidly for tomographic diagnosis or treatment comprises a head cradle having a base portion (10) and an upwardly-extending boss (12) with a concave portion (20) in the center thereof. The concave portion has a plurality of holes (22) therein and a chamber (24) thereunder. A vacuum hose (38,40,46) is in communication with the chamber. The upper rim of the cradle has a resilient sealing ring (14). A patient's head may be placed in the cradle and the chamber partially evacuated, whereby the patient's head can be held against the rim by the vacuum. A repositioning device can be used to obtain the patient's position so that the patient can be repositioned for a later treatment or diagnosis. The repositioning device comprises a mouthpiece (60) which can be unambiguously attached to the patient's head and an adjustable level (52) which can be attached to the mouthpiece in an unambiguous manner. After the patient's head is positioned, the level is adjusted to indicate a level condition. Then at a later session the positioning device is reinserted in the patient's mouth and the patient's head is adjusted until the level indicates a level condition, whereupon the patient's head will be positioned precisely in its former position. The vacuum is then applied to lock the patient's head in the former position.

9 Claims, 2 Drawing Sheets

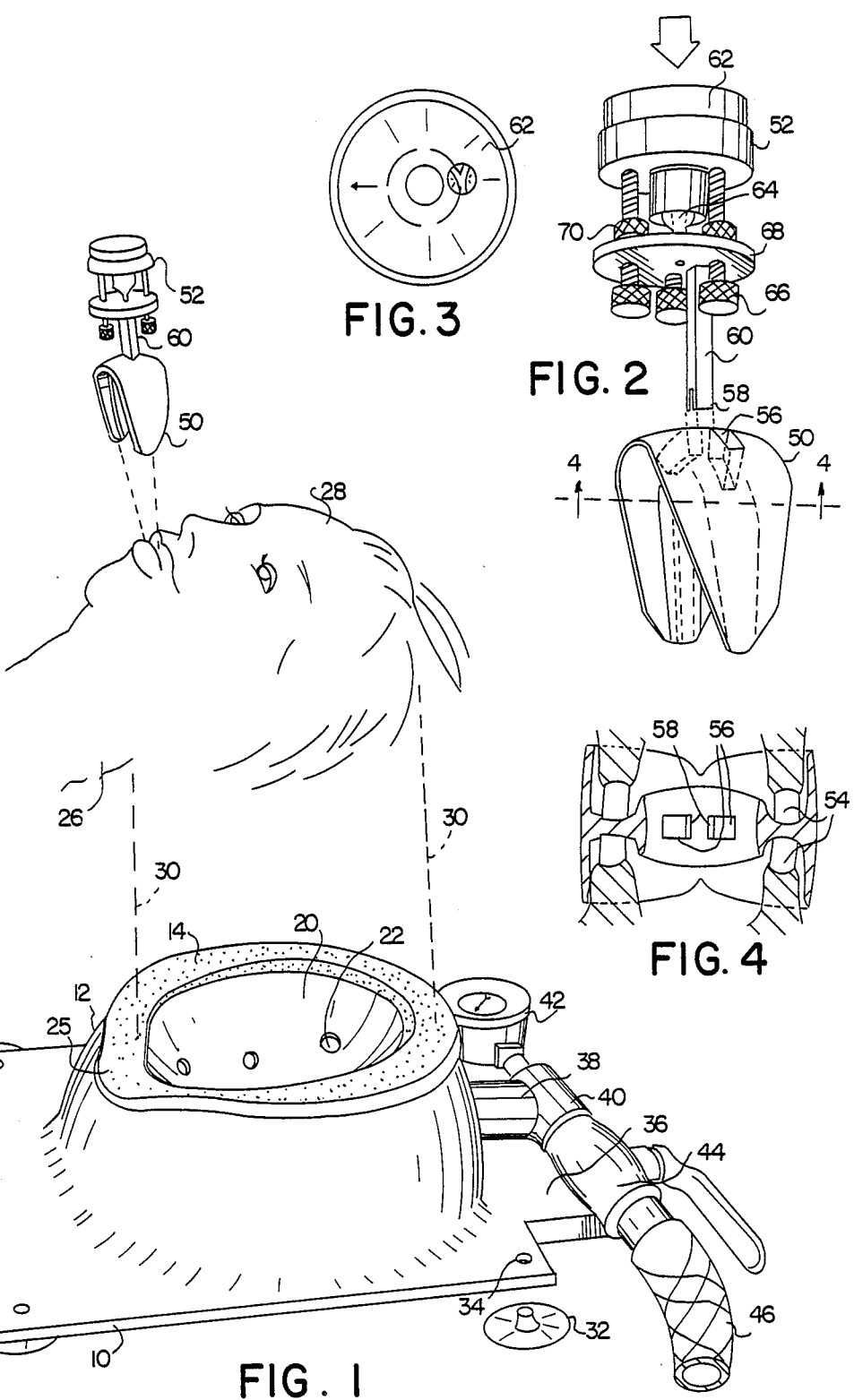

ANIMAL-HOLDING AND POSITION RESTORING DEVICE EMPLOYING VACUUM HOLDER AND MOUTHPIECE LEVEL

This application is a continuation of Ser. No. 670,898, filed Nov. 13, 1984, now abandoned.

BACKGROUND

1. Field of Invention

This invention relates to the field of medical apparatus, particularly to a medical device for immobilizing a patient's head during treatment or examination by tomographic or X-ray apparatus or the like. Also the head immobilizer of the invention can be used to position a patient's head in any precise position, identical to a previously-held position.

2. Description of Prior Art

During certain medical treatments and examinations of a patient, his or her head must be held in a fixed, rigid position. Specifically the head, or another part of a patient's anatomy, must be held very rigidly during the following exemplary types of procedures: surgical procedures, including dentistry, emergency medical care, physical and occupational therapy, tomographic examinations (multiple X-rays taken using a CAT (computer axial tomography) scanner, NMR (nuclear magnetic resonance) tomographic scanner examinations ("pictures" taken in a similar fashion), X-ray malignancy treatment procedures (radiation beams directed at a focus in the body from a plurality of angles), etc. This is because tomographic and similar processes involve patient irradiations or the taking of multiple pictures from many angles over a period of time, usually a few minutes, to enable a computer to provide a composite cross section of the head. If the head (or other anatomical part) is allowed to move during the process, the resultant cross-sectional picture will be distorted and blurred and of little medical value.

Heretofore various methods and devices were used to immobilize the head for these processes.

In some, the head was cradled in a form-fitting rest. However such cradles or rests left much to be desired since they did not hold the head rigidly and thus the patient could easily move it during the process.

In others, the head was clamped, either from top to bottom, side to side, in the mouth, or with a combination of these methods. While such clamps could immobilize the head, they were usually extremely uncomfortable for the patient since force from the clamps, when applied for an extended period of time, caused trauma to the patient. If the clamps were padded sufficiently to avoid trauma, they then were too resilient to hold the patient rigidly.

In still others, a clamping device was actually screwed into the patient's head, usually the cheekbones, under surgical anaesthesia. While this device held the patient's head in a very immobile manner, patients obviously found it extremely traumatic, painful, disfiguring, and uncomfortable.

In a further device, the patient was held by an air-impedance sheet draped over the patient's torso, which sheet was held in position against the patient by a vacuum source in communication with the underside of the sheet. This device did not fully immobilize the patient and also it was not feasible to use it to hold a patient's head because the sheet would block the patient's nose or mouth.

In addition to their foregoing disadvantages, most of the aforementioned devices also suffered from a lack of position repeatability. I.e., if the physician desired to reposition the patient in precisely the same position as previously used for a repeat treatment or diagnosis, e.g., for checking the patient's progress after treatment or for repeating a therapeutic treatment, most of the aforementioned devices could not be used to reposition the patient in precisely the same position in which he or she was previously held.

In addition to holding the head for medical procedures, other applications exist where the body or parts thereof must be held rigidly or immobile without discomfort or trauma. E.g., in land, sea, air, or space vehicles, the head and/or the body must be held securely during positive and negative accelerations, e.g., when starting, stopping, in case of crashes, etc.

OBJECTS AND ADVANTAGES

Accordingly several objects and advantages of the invention are to provide a head immobilizing device which is very comfortable, which is easy to use, which is simple in operation, which holds the patient's head rigidly, which does not cause trauma, which does not require surgery, which does not disfigure the patient, which does not block the patient's breathing, and which can be used to reposition a patient's head in precisely the same position as it was previously held by the device. Further objects and advantages will become apparent from a consideration from the ensuing description and accompanying drawings.

DRAWING FIGURES

On the first of the two sheets of drawings:

FIG. 1 is a perspective exploded view of a head immobilizing and positioning device and patient according to the invention.

FIG. 2 is an elevational view of a mouthpiece positioning assembly of FIG. 1;

FIG. 3 is a top view of a level of such assembly; and

FIG. 4 is a cross-sectional view of such assembly in position in a patient's mouth, taken along the lines 4—4 of FIG. 2.

On the second sheet of drawing:

FIG. 5 is a top view of the head-holding device;

FIG. 6 is a side sectional view of the device taken along the lines 6—6 of FIG. 5;

FIG. 7 is a back-to-front sectional view taken along the lines 7—7 of FIG. 5; and FIG. 8 is a front-to-back sectional view taken along the lines 8—8 of FIG. 5.

Figure 5:
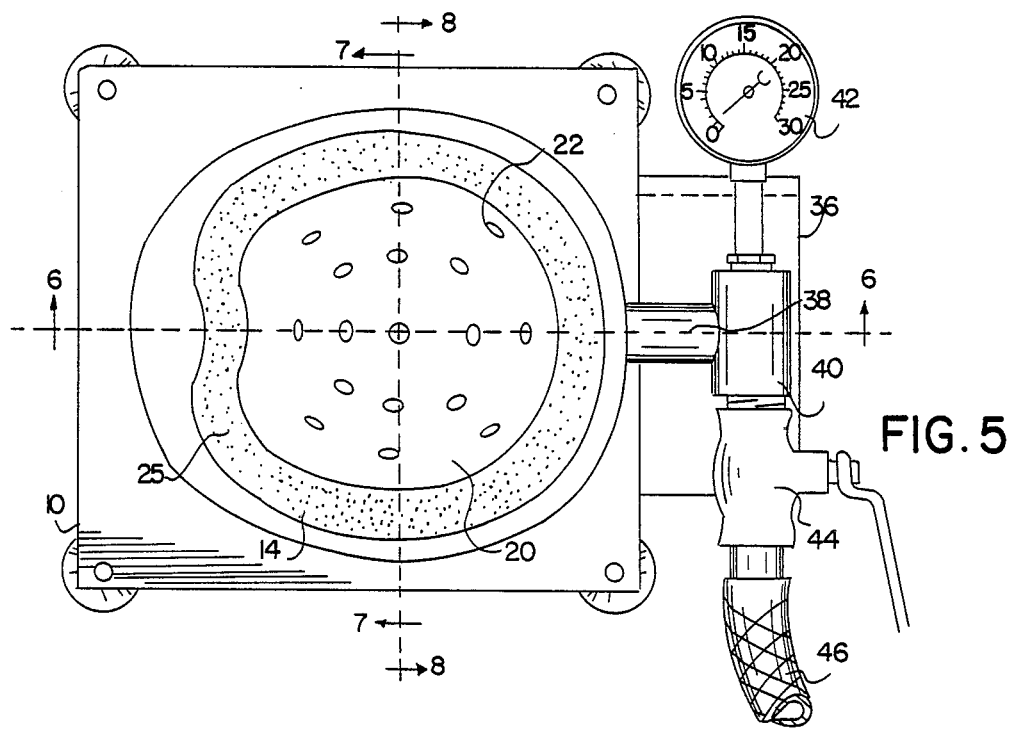

DRAWING REFERENCE NUMERALS 10 base
12 boss
14 foam ring
16 bottom plate
18 upper portion
20 concave portion
22 hole
24 chamber
25 neck depression
26 neck
28 patient's head
30 broken line
32 suction cup
34 hole
36 apron 38 vacuum coupling
40 T-fitting
42 gauge
44 valve
46 hose
50 mouthpiece
52 positioning gauge
54 teeth
56 holes
58 fingers
60 leg
62 level
64 center pivot
66 thumbscrews
68 baseplate
70 locknuts.

DESCRIPTION OF HEAD-IMMOBILIZING DEVICE

The head-immobilizing device of the invention comprises a head cradle in which the back of the head rests and to which it is securely held by actually applying a vacuum to the interior of the cradle to enable ambient air pressure to press the head thereto in a highly-uniform manner.

As shown in perspective view in FIG. 1, the head-cradling device comprises a flat base 10, preferably of polystyrene, having a boss or upwardly-extending cup-shaped portion 12 which is open at the top. The rim of boss 12 is covered by a cushioning and sealing ring 14 of foam rubber or the like having a high conformance resolution ability, preferably the foam sold under the mark TEMPER FOAM by Kee-Gee, Inc. Ring 14 provides at least a partially-airtight circumferential seal around the back of a patient's head, as will be described. Base 10 measures about 35 cm by 25 cm overall and boss 12 is about 9.5 cm high. The other dimensions are scaled approximately as shown in the figures.

Figure 6:
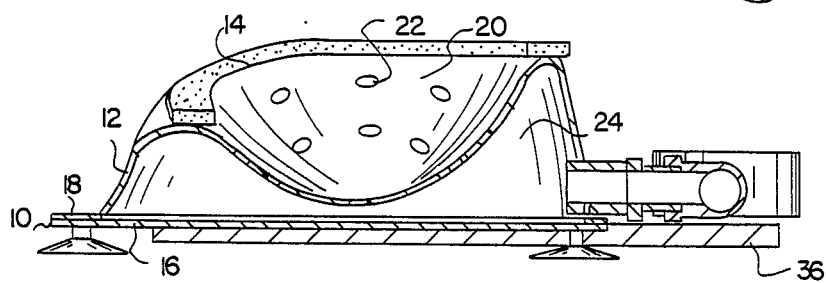
Figure 7:
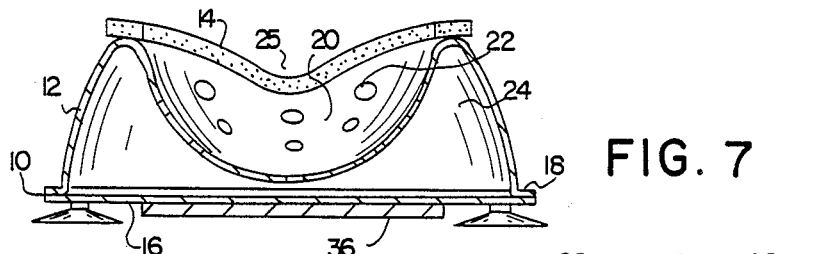
Figure 8:
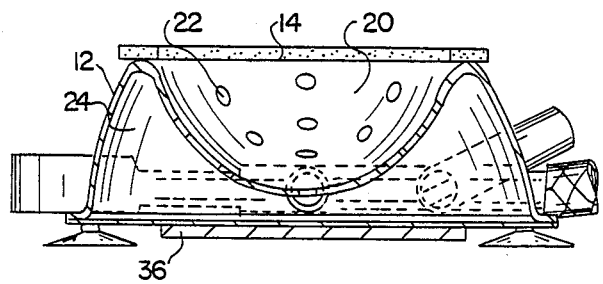

Base 10 comprises (FIGS. 6 to 8) a flat, imperforate bottom plate 16 and an upper portion 18 which is flat around its periphery where it is joined to the periphery of bottom plate 16, e.g., by solvent cement. Upper portion 18 curves up to form boss 12 and then, after forming a rim under ring 14, curves down and inwardly to form a concave portion 20. Concave portion 20 has a plurality of holes or perforations such as 22 and extends down to but does not reach bottom plate 16, as indicated in FIGS. 6 to 8. A chamber 24 is thereby formed between bottom plate 16 and boss portion 12. The front part of the rim of the device under ring 14, i.e., the left side of the rim in FIGS. 1 and 6, curves down to form a neck depression 25; this depression has a lower height than the rest of the rim so as to accommodate the neck portion of a patient's head 28 when said patient places the back of his or her head onto ring 14 and into the device in the direction indicated by lines 30.

Base 10 is firmly held to a gurney or table (not shown) by any suitable means, such as four suction cups, e.g., 32, which have upwardly-extending legs which extend through four corner holes (such as 34) of base 10. Alternatively, base 10 may be clamped to the table, or it may be bolted, vacuum held, or even adhesively glued. As a further alternative, base 10 or the entire device may be integrally formed with the table, gurney, or platform.

Base 10 is generally square in shape, as indicated in the top view of FIG. 5, except for a rectangularly-shaped apron portion 36 which extends back about 10 cm from the rear edge of base 10 and which also extends partially under base 10, as indicated in FIG. 6, to rigidify such base. Above apron 36 is a vacuum coupling 38, which is a simple outlet in patent communication with chamber 24, as indicated in FIG. 6. Coupling 38 may be integral with boss portion 18, or it may be clamped or bolted thereto. The free end of coupling 38 is jointed to a "T" fitting 40 which communicates to a vacuum pressure gauge 42 and to a valve 44 which in turn communicates to a flexible hose 46. Hose 46 is connected to an adjustable vacuum source (not shown). Alternatively, parts 38, 40, 42, and 44 may be mounted away from the head holder, e.g., adjacent the vacuum source (not shown), or even in another room. The vacuum source should be able to create and maintain a vacuum of about 7 to 13 cm of Hg.

DESCRIPTION OF POSITIONING DEVICE

The head-immobilizing device aforedescribed will hold a patient's head rigidly, in the manner to be described infra. However, as noted, physicians often also have a need to reposition a patient's head in the same position for multiple diagnostic examinations and treatments over a period of time. For this purposes the positioning device shown in FIG. 1 and FIGS. 2 to 4 may be used.

The positioning device comprises a mouthpiece 50 and an attachable positioning gauge 52 which is attachable to mouthpiece 50. Mouthpiece 50 comprises a rigid, but yieldable member, preferably of moldable, low-molecular-weight polyethylene, which has two grooves which are shaped to fit between the patient's upper and lower teeth 54, as indicated in FIG. 4. Mouthpiece 50 also has two rectangular holes 56 in its upper surface for receiving the bottom fingers 58 of leg 60 of gauge 52.

Gauge 52 comprises a circular fluid-filled level 62 (FIG. 3) having a conventional air bubble and a centering circle. Level 62 is pivotably mounted on a center ball-and-socket pivot 64 and its angular orientation is adjustable by means of three lockable thumbscrews, such as 66, which are threaded onto a base plate 68 and which have respective locknuts such as 70. Mounting leg 60 is attached to and extends down from base plate 68, and, as stated, has two fingers 58 which are shaped to engage and mate with holes 56 of mouthpiece 50, as indicated in FIG. 4.

OPERATION—HEAD IMMOBILIZING DEVICE

In operation, with the vacuum off, the back of the head of a patient 28 is positioned onto the head cradle, against faom ring 14, with the patient's neck 26 in front depression 25 of ring 14, in the manner indicated by lines 30 of FIG. 1. The patient's head is adjusted to the desired position, generally facing straight up. Then the vacuum is applied to chamber 24, either by turning on the vacuum apparatus or by opening valve 44.

When the vacuum reaches the desired level, generally about 10 cm of Hg, in chamber 24, as indicated by gauge 42, the patient's head will be firmly, but comfortably held to the device by the pressure differential between the bottom of the patient's head and the rest of the head, due to the partial vacuum behind the head from chamber 24 which communicated with the back of the patient's head via holes 22.

Although the seal between the patient's head and ring 14 will not be perfect, and hence some air may leak into the device between ring 14 and the patient's head, I have found that the patient's head will still be held firmly and in an immobile manner, yet quite comfortably to the device. The patient's head will be pressed against ring 14 and will not touch the floor of concave portion 20. Although the patient will not be able to move his or her head, no trauma or painful force will be sensed by the patient because the holding force is evenly distributed by the pressure differential around the relatively large area of ring 14. Moreover I have found that the device will work quite satisfactorily even if the patient has long hair.

When the medical procedure is over, the vacuum is released, either by turning off the vacuum source or opening valve 44. Thereupon the patient's head will be freed and it can be lifted up and away from the device. No bruises, pressure marks, or any other adverse effects will result.

OPERATION—POSITIONING DEVICE

If the physician desires to hold the patient in precisely the same position at a later date, the positioning device of FIGS. 2 to 4 should also be used to fix the patient's position. Once the patient is in the desired position, the positioning device is inserted into the patient's mouth and the patient is instructed to clamp the device between his or her teeth or gums, as indicated in FIG. 4. When this has been done, mouthpiece 50 will be fixed to the patient's head in an unambiguous manner.

Then thumbscrews 66 of positioning gauge 52 are adjusted as necessary to bring the bubble of level 62 into the center circle, whereafter the thumbscrews are locked in position by their locknuts 70. At this time the vacuum is actuated to lock the patient's head in position. The positioning gauge can then be removed, labeled with the patient's name, and stored until the patient's next visit.

When the patient visits again, the mouthpiece is inserted between the patient's teeth or gums with gauge 52 attached. The patient's head is adjusted until the bubble in the level is centered, whereupon the patient's exact former position will be reached. Then the vacuum is applied to lock the patient's head in the same position once again. The process can be repeated as many times as necessary.

SUMMARY, SCOPE, AND RAMIFICATIONS

The reader will thus note that a trauma-free, highly comfortable, simple, reliable, accurate, and relatively inexpensive means of holding a patient's head has been provided. A vacuum-holding procedure can be applied directly to a portion of the person's body without trauma, discomfort, etc., yet with the ability to create a very rigid securement.

While the above description contains many specificities, these should not be construed as limitations upon the scope of the invention, but as an examplification of one preferred embodiment thereof. Many other embodiments are feasible within its scope. For example, in lieu of holding a patient's head, a device can be fabricated with a suitable shape to hold any other portion of a patient's body, such as a torso, leg, arm, etc. The device can be made of a wide variety of materials in shapes other than as shown. The positioning device can be attached to a part of a person's anatomy other than the teeth. Also it can be used with non-human animals. The device can be used for non-medical procedures, e.g., to hold an actor's head for the application of makeup, to hold palsied persons for examination, photography, etc. In lieu of a two-part base, the entire device can be formed of a single piece of plastic, or the lower part 16 of the base can be the table and the upper part 18 thereof can be glued to the table. The vacuum fitting can be attached underneath the device, rather than at the rear thereof. Accordingly the full scope of the invention should be determined by the appended claims and their legal equivalents, and not by the examples given.

I claim:

1. An animal-holding and accurate repositioning apparatus, comprising:
   (a) holding means comprising a rigid, airtight chamber, except for an open portion on one side thereof, and an airway on another side thereof, said open portion having an edge which forms a circumferential seal which is shaped to mate conformingly with a predetermined portion of an animal's anatomy so as to provide at least a partially airtight circumferential seal around said predetermined portion of said animal's anatomy,
   (b) mounting means for fixing said holding means in a rigid position,
   (c) vacuum means connected to said airway for controllably creating and maintaining a partial vacuum in said chamber and adjacent said predetermined portion of said animal's anatomy circumscribed by said circumferential seal, whereby said partial vacuum in said chamber will enable ambient air pressure against the portion of said animal not circumscribed by said seal to hold said animal tightly against said holding means and hence fixed in a rigid position, and
   (d) means for remembering the position of said animal's anatomy as held by said holding means after said animal is removed from said holding means and for indicating when said position is accurately restored after said animal is again held by said holding means.

2. The animal-holding device of claim 1 wherein said means for remembering comprises an adjustable level and means for attaching said level to said portion of said animal's anatomy in an unambiguous manner, and further including means for adjusting said level so that a level condition is indicated after said level is so attached to said animal.

3. The animal-holding device of claim 2 wherein said holding means comprises a head cradle and said means for remembering also comprises a mouthpiece and means for removably attaching said mouthpiece to said level.

4. The animal-holding device of claim 3 wherein said means for removably attaching said mouthpiece to said level is arranged to removably attach said mouthpiece to said level in an unambiguously rejoinable manner.

5. Head-immobilizing and position-restoring apparatus for an animal, comprising:
   (a) a base portion having a head cradle, said head cradle being rigid and shaped to receive the back of an animal's head and form at least a partial vacuum circumferential seal around the back of said animal's head, said cradle including a vacuum chamber in communication with the portion of said animal's head circumscribed by said seal,
   (b) means for creating and maintaining at least a partial vacuum in said chamber adjacent the back of said animal's head so as to cause said head to be held against said cradle by air pressure, (c) mounting means for holding said cradle in a fixed position, and (d) means for remembering the position of said animal's anatomy as held by said head cradle after said animal is removed from said head cradle and for indicating when said position is accurately restored after said animal is again held by said head cradle.

6. The animal-holding device of claim 5 wherein said means for remembering comprises and adjustable level and means for attaching said level to said animal's head in an unambiguous manner, and means for adjusting said level so that a level condition is indicated after said level is attached to said animal's head.

7. The animal-holding device of claim 6 wherein said means for remembering also comprises a mouthpiece.

8. The animal-holding device of claim 7, further including means for separating and rejoining said mouthpiece to said level in an unambiguous manner.

9. An accurate heat-positioning device for an animal, comprising, in combination:

(a) attachment means comprising a mouthpiece which can be rigidly positioned between the teeth or gums of said animal's body in an unambiguous and repeatable position, (b) a level for providing an indication when said level is in a level position, said level being removably attached to said mouthpiece, (c) adjustment means for adjusting the position of said level with respect to said mouthpiece, when said mouthpiece is positioned between said teeth or gums in said unambiguous position, until said level indicates a level position, (d) means for locking said level in its level position, as adjusted with respect to said mouthpiece, and (e) means for holding said head of said animal's body in a rigid position after said level is adjusted, whereby said level can be adjusted to a level position by said adjustment means when said attachment means is attached to said animal's head, whereafter adjustment of the position of said animal's head to a position where said level is in a level position will cause said animal's head to be in the same position as it was initially.

* * * * *

UNITED STATES PATENT AND TRADEMARK OFFICE
CERTIFICATE OF CORRECTION

PATENT NO. : 4,841,965

DATED : June 27, 1989

INVENTOR(S) : Jacobs, D. A.

It is certified that error appears in the above-identified patent and that said Letters Patent is hereby corrected as shown below:

Col. 1 , l. 62, change "impedance" to --impermeable--.

Claim 9, l. 1, change "heat" to --head--.

Signed and Sealed this

Thirteenth Day of March, 1990

Attest:

JEFFREY M. SAMUELS

*Attesting Officer*      *Acting Commissioner of Patents and Trademarks*